United States Patent [19]

Chinol et al.

[11] Patent Number: 5,902,566
[45] Date of Patent: *May 11, 1999

[54] PROCESS FOR PRODUCING YTTRIUM-90-LABELLED PROTEIN SUBSTRATE

[75] Inventors: Marco Chinol, Whitestone, N.Y.; Rodolfo Franceschini, Romano Canavese; Fabio Lunghi, Moncrivello, both of Italy

[73] Assignee: Ministero Dell 'Universita' E Della Ricerca Scientifica E Tecnologica, Italy

[ * ] Notice: This patent issued on a continued prosecution application filed under 37 CFR 1.53(d), and is subject to the twenty year patent term provisions of 35 U.S.C. 154(a)(2).

[21] Appl. No.: 08/630,194

[22] Filed: Apr. 10, 1996

Related U.S. Application Data

[63] Continuation of application No. 08/088,310, Jul. 7, 1993, abandoned.

[30] Foreign Application Priority Data

Jul. 10, 1992 [IT] Italy ................... TO92A0592

[51] Int. Cl.$^6$ ................... A61K 51/00
[52] U.S. Cl. ............ 424/1.49; 424/1.11; 424/1.69; 534/10; 250/432 PD; 423/2
[58] Field of Search ............... 534/10; 422/238; 250/432 PD; 424/1.11, 1.69, 1.49; 530/391.3

[56] References Cited

U.S. PATENT DOCUMENTS

| | | | |
|---|---|---|---|
| 3,156,532 | 11/1964 | Doering et al. | 534/10 |
| 5,225,173 | 7/1993 | Wai | 423/2 |
| 5,729,821 | 3/1998 | Knapp et al. | 424/1.11 |
| 5,744,119 | 4/1998 | Phillips | 424/1.49 |

FOREIGN PATENT DOCUMENTS

| | | |
|---|---|---|
| 2068656 | 11/1970 | France . |
| 8601407 | 3/1986 | WIPO . |

OTHER PUBLICATIONS

Minami et al, Bull. Chem. Soc. Japan, vol. 31, pp. 372–377, (1958).

Chemical Abstracts, 1969.

Int. J. Appl. Rad. Isot, (vol. 29, No. 2, "A New SR90/Y90 Radioisotope Generator", 1978.

Int. J. Appl. Rad. Isot. (vol. 36, No. 10, "The Production and Biological Distribution of Yttrium–90 Labelled Antibodies", 1985.

J. Nucl Med 28; 1465–1470, 1987.

European Journal of Nuclear Medicin, vol. 15, No. 6, 1989.

*Primary Examiner*—Philip Tucker
*Attorney, Agent, or Firm*—Rogers & Wells LLP

[57] ABSTRACT

A process for the production of yttrium-90, generated by radioactive decay of strontium-90, by means of a generator including a column containing strontium-90 adsorbed on a cation-exchange resin, wherein yttrium-90, the decay product of strontium-90, is obtained by the flow of an eluent through the resin column of the generator, an acetate buffer solution being used as the eluent. The process enables a solution to be obtained which is usable directly for labelling protein substrates, particularly monoclonal antibodies, with yttrium-90.

7 Claims, No Drawings

PROCESS FOR PRODUCING YTTRIUM-90-LABELLED PROTEIN SUBSTRATE

This application is a continuation of Ser. No. 08/088,310 filed Jul. 7, 1993, now abandoned.

The present invention relates to a process for the production of yttrium-90 by means of a generator. Yttrium-90 ("daughter" radionuclide) is a product of the radioactive decay of strontium-90 ("parent" radionuclide).

Yttrium-90 is considered to be one of the most useful and important radionuclides in radioimmunotherapy. This radionuclide has a half-life (64 hours) compatible with the uptake rate of the antibody in the tumour. More particularly, data from the literature show that the monoclonal antibodies (MoAb) may be labelled with yttrium-90 by means of suitable DTPA (diethylenetriaminepenta-acetic acid) groups previously conjugated with the monoclonal antibody. Yttrium-90 is moreover a pure emitter of high-energy beta-particles (Emax 2.3 MeV). All these properties of yttrium-90 have thus resulted in its widespread use in the treatment of tumours in association with specific monoclonal antibodies.

Obviously, to label the MoAb, the yttrium-90 solution must be of high chemical, radiochemical, and radionuclide purity with proper values of radioactive concentration.

Yttrium-90 is produced by a generator via the radioactive decay of strontium-90 ($^{90}Sr$) (parent radionuclide). The nuclear characteristics of the $^{90}Sr/^{90}Y$ system are given below:

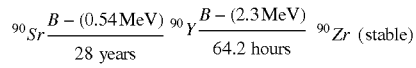

Although numerous at generators have been developed and described, most of the clinical trials with $^{90}Y$-MoAb have been carried out with yttrium-90 obtained from commercial sources. The use of a generator and the development of methods for labelling MoAb with yttrium-90 obtained from a generator have clearly reduced the cost of this radionuclide and also offer the advantage of providing the required activity when necessary. $^{90}Sr/^{90}Y$ generators have been reported in the literature, for example in U.S. Pat. No. 3,156,532 and J.Nucl.Med. 28, 1465–1470, 1987.

Various methods are reported in the literature for eluting the cation-exchange column on which strontium-90 is adsorbed; these use lactate, oxalate, citrate and EDTA as eluents. The common drawback is that yttrium-90 is not eluted in the ionic form which is the optimum form for labelling conjugate-DTPA protein substrates.

The concentration of the chelating and complexing agents present in the eluate was found to cause competition with the DTPA groups which dramatically reduces the labelling efficiency. Consequently it is necessary to remove these agents before labelling protein substrates so as to avoid the need for post-labelling purification.

An object of the present invention is to overcome this problem by means of a commercial yttrium-90 generator in a form suitable for direct labelling of monoclonal antibodies.

To this end, the subject of the invention is a process for the production of yttrium-90 by radioactive decay of strontium-90, employing a generator where strontium-90 is adsorbed on a cation-exchange resin column wherein yttrium-90, product of the decay of strontium-90, is eluted by the flow through the generator column of an acetate buffer solution used as the eluent.

Preferably the solution has a molar concentration ranging from 0.5 to 0.8M (pH 5.0–5.5).

By means of the process of the invention, yttrium-90 is obtained from the generator in quantitive yields and in volumes of less than 20 ml and hence with a radioactive concentration sufficient for the effective labelling of monoclonal antibodies.

The use of the eluent and such a narrow range of pH values has further significant advantages. In the first place, by operating within this pH range, yttrium-90 can be recovered quantitatively from the generator, thus reducing the breakthrough of strontium-90 to a minimum. This result is demonstrated in the following table which shows the effect of pH on the adsorption of strontium-90 and yttrium-90 on the cation-exchange resin AG50-WX16 column (Bio-Rad) (200–400 mesh, $Na^+$ form).

| pH  | $^{90}Sr$ adsorption | $^{90}Y$ adsorption |
|-----|----------------------|---------------------|
| 1.5 | 100                  | 100                 |
| 3.5 | 100                  | 14                  |
| 3.7 | 100                  | 10                  |
| 4.6 | 100                  | <1                  |
| 5.5 | 100                  | <1                  |
| 7.0 | <1                   | <1                  |

Yttrium-90, as acetate salt, can easily be separated from its parent ($^{90}Sr$) by chromatography, for example, by thin-layer chromatography. This makes the checking for $^{90}Sr$-breakthrough, and hence also for the radionuclide purity of the eluent, quick and simple.

Moreover, yttrium-90 acetate may be used directly for MoAb labelling.

The generator for carrying out the process of the invention may be produced on an industrial scale by following known technology and operating processes for the production of known $^{99}Mo/^{99m}Tc$ generators. The entire system is safe, easy to transport and may be used by any radiopharmacy laboratory technician within a nuclear medicine centre. The generator provides a sterile and pyrogen-free eluate which is usable directly for in vivo clinical trials in man. To advantage, the generator of the invention includes a first column containing a cation-exchange resin on which strontium-90 is adsorbed and a second, safety column, in series with the first and containing the same cation-exchange resin originally free from strontium-90. This second column is connected to the first one immediately after its filling with the resin on which strontium-90 is fixed. Consequently any traces of strontium-90 which may be eluted from the first column are adsorbed by the second column, ensuring that the eluate is free from any strontium-90 trace.

This technical expedient is very important in evaluating quality of the generator with time. In fact, self-radiation or similar phenomena may, in time, alter the efficiency of strontium-90 link to the resin column, with consequent increase in strontium-90 breakthrough in the eluate. This is of paramount importance given the nuclear characteristics and toxicity of this radionuclide.

Thus the use of the second column in series with that containing strontium-90 causes a significant increase in the shelf life of the generator. This reduces cost, while at the same time ensuring the quality of the eluate, which is of fundamental importance for its in vivo use in man. The preferred cation-exchange resins are obtained by the sulphonation of divinylbenzenestyrene copolymers, available as $H^+$, $Na^+$ or $NH_4^+$ form. Preferably resins of the type indicated above and with a high degree of cross-linking are used, such as the resin AG50-WX16, with 16% cross-linking, converted into sodium salt (200–400 mesh).

EXAMPLE

A generator of the type described above is used including first and second columns in series containing the resin AG50-WX16 (Bio-Rad), indicated above. A 0.6M acetate buffer solution is used as eluent; 20 ml of this solution are eluted through the columns over a period of one to two minutes.

The eluate collected is analyzed by thin-layer chromatography and shows complete absence of strontium-90.

0.5 ml of eluate (yttrium-90 acetate) containing about 0.15 mCi of yttrium-90 are added to 0.1 mg of MoAb previously conjugated with DTPA (2.3 groups of DTPA/mole of antibody). The reaction time is 15 minutes; labelling is carried out at room temperature. The preparation is purified by dialysis or gel filtration chromatography (phosphate buffer at pH 7.0 as eluent). The labelling yield is on average 90±5%.

We claim:

1. A process for obtaining $^{90}Y$ in ionic form and directly labelling a protein substrate with said $^{90}Y$ in ionic form, which process comprises the steps of (a) providing a column consisting of a cation exchange resin having adsorbed thereto $^{90}Sr$, (b) eluting the column with an eluent consisting of an acetate buffer solution having a pH of from 4.6 to 5.5, free of organic solvent and chelating agent to selectively elute $^{90}Y$ formed by the decay of the $^{90}Sr$ adsorbed to the cation exchange resin; (c) recovering the $^{90}Y$ acetate eluate so formed; and (d) labelling a protein substrate using without further treatment the $^{90}Y$ acetate eluate from step (c).

2. The process of claim 1, wherein the acetate buffer solution has a molar concentration of from 0.5M to 0.8M, and a pH of from 5.0 to 5.5.

3. The process of claim 1, wherein the cation exchange resin is obtained by the sulphonization of a polystyrene-divinylbenzene copolymer.

4. The process of claim 1, wherein the volume of the eluent passed through the column is less than 20 ml.

5. The process of claim 1, further comprising the step of passing the $^{90}Y$ acetate eluate recovered in step (b) through a second column prior to step (c), said second column comprising a cation exchange resin free of $^{90}Sr$.

6. The process of claim 1, wherein the protein substrate is a monoclonal antibody.

7. The process of claim 6, wherein the monoclonal antibody is conjugated with diethylenetriamine penta-acetic acid groups prior to labelling in step (c).

* * * * *